United States Patent [19]
Babington et al.

[11] 4,202,897
[45] May 13, 1980

[54] PROLACTIN SECRETION INHIBITORS

[75] Inventors: Ronald G. Babington, Denville; F. Eugene Harrington, Mendham, both of N.J.

[73] Assignee: Sandoz, Inc., E. Hanover, N.J.

[21] Appl. No.: 904,191

[22] Filed: May 11, 1978

Related U.S. Application Data

[63] Continuation-in-part of Ser. No. 891,299, Mar. 29, 1978, abandoned, which is a continuation-in-part of Ser. No. 862,366, Dec. 20, 1977, abandoned, which is a continuation-in-part of Ser. No. 818,420, Jul. 25, 1977, abandoned.

[51] Int. Cl.² .................. A61K 31/495; A61K 31/47; A61K 31/48
[52] U.S. Cl. .................................... 424/250; 424/258; 424/260; 424/261; 424/262; 424/273 R
[58] Field of Search .................. 424/273 R, 258, 250, 424/260, 261, 262

[56] References Cited

U.S. PATENT DOCUMENTS 3,852,303  12/1974  Houlihan ........................... 260/309.6

OTHER PUBLICATIONS

Chem. Abst. 9th Col. Index, vol. 76–85 (1972–1976), pp. 19265cs, 19267cs and 19268cs.

*Primary Examiner*—Sam Rosen
*Attorney, Agent, or Firm*—Gerald D. Sharkin; Robert S. Honor

[57] ABSTRACT

Certain known imidazo[2,1-a]isoindoles and isoquinolines, e.g., 5-(p-chlorophenyl)-5-hydroxy-2,3-dihydro-5H-imidazo[2,1-a]isoindole (mazindol), have been found to be useful as inhibitors of prolactin secretion, and may be so utilized alone or as an agent which enhances the action of other chemical compounds having activity in inhibiting prolactin secretion.

21 Claims, No Drawings

PROLACTIN SECRETION INHIBITORS

This application is a continuation-in-part of application Ser. No. 891,299, filed Mar. 29, 1978, which in turn is a continuation-in-part of application Ser. No. 862,366, filed Dec. 20, 1977, which in turn is a continuation-in-part of application Ser. No. 818,420, filed July 25, 1977, all now abandoned.

This invention relates to the use of known substituted imidazo[2,1-a]isoindoles and imidazo[2,1-a]isoquinolines alone or in admixture with other active agents in inhibiting the secretion of prolactin.

The active isoindoles and isoquinolines with which this invention is concerned may be reresented by the following structural formula

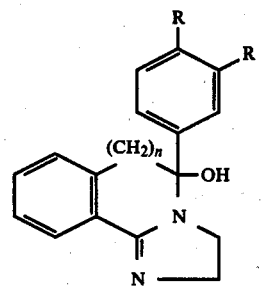

where
n represents 0 or 1,
each R, independently, represents hydrogen or halo of atomic weight about 19 to 36,
or a pharmaceutically acceptable acid addition salt thereof.

As will be appreciated by persons skilled in this art, some of the acid addition salt forms of the compounds (I) may actually involve a tautomeric or modified form of the above structure in salt form, but in order to simplify this description, and although both forms are intended to be included, reference will only be made in the specification and claims to the compounds (I) and salts thereof.

One aspect of this invention concerns the use of compounds (I) alone in inhibiting prolactin secretion. A further aspect of this invention contemplates the use of said compounds (I) in enhancing the prolactin secretion inhibition activity of other compounds, hereinafter generically referred to as "secondary active agents." These secondary active agents comprise compounds which are found to be useful in inhibiting the secretion of prolactin in mammals, and include ergocryptines such as ergocryptine and 2-bromo-α-ergocryptine (the latter being preferred), ergolines such as lergotrile, lisuride, 8α-cyanomethyl-6-methylergoline, 6-methyl-8β-(2-pyridyl-thiomethyl)-ergoline, and 6-methyl-8α-(N,N-dimethylsulphamoylamino)-ergoline, piribedil and apomorphines such as apomorphine.

A preferred aspect of this invention involves the above-indicated use of the compounds (I) at surprisingly low dosages to accomplish the desired inhibition of prolactin secretion. More preferred is use of compounds (I) alone at this low dosage.

The compounds of formula (I) are known and may be prepared according to methods disclosed in various patents and publications in the United States and foreign countries, e.g., The Journal of Organic Chemistry, 33, No. 7, July 1968, pp. 2874–2877. The present invention contemplates only the novel use of such compounds either alone or in conjunction with the secondary active agents, particularly as agents useful in inhibiting prolactin secretion in mammals. The imidazo[2,1-a]isoindoles are preferred, whereas the preferred compound for this use is 5-(p-chlorophenyl)-5-hydroxy-2,3-dihydro-5H-imidazo[2,1-a]isoindole (mazindol).

The secondary active agents may be prepared by methods disclosed in the art. Respecting 2-bromo-α-ergocryptine, its method of preparation is taught in U.S. Pat. No. 3,752,814, dated Aug. 14, 1973.

The compounds of formula (I) and the combinations referred to herein are useful as prolactin inhibitors as indicated by noting serum levels of prolactin after oral administration to rats of 0.25 mg/kg of active agent. Thirty male albino Wistar rats weighing 150–200 grams are used to determine the effects of drug on serum levels of prolactin. The drug is administered per os in 0.5% carboxy methyl cellulose at 0.25 mg/kg of animal body weight. Eighteen males were used as controls and the remaining twelve test animals are treated with the active agent.

At the time of drug administration six control rats are sacrificed by decapitation. At 30 and 60 minutes following drug treatment groups of six controls and animals treated with the drug are also sacrificed by decapitation. Blood samples are collected at autopsy, allowed to clot and the serum separated by centrifugation. Serum samples are assayed using radioimmunological techniques disclosed by Niswender, G. D., et al., Proc. Soc. Exper. Biol. & Med. 130:793, 1969; and Neil, J. J. et al., Endocrinology 88:548, 1971.

Results of the study demonstrated that active agent at the dose investigated inhibits prolactin secretion as evidenced by the low serum levels of prolactin. Furthermore, this effect is noted in some instances as late as 60 minutes following treatment.

The surprising and unobvious effect of the compounds (I) of this invention in inhibiting prolactin secretion, either alone or to enhance such activity of other compounds, can be explained in part as follows. Prolactin is released from the anterior pituitary gland. Release of prolactin from the pituitary is restricted by a Prolactin Inhibitory Factor (PIF) that is believed to be dopamine [Endocrinology, 94, 1077 (1974)]. Various chemical agents are believed to affect PIF activity in the pituitary. And these chemical agents are believed to act in three different ways and may therefore be placed into three different categories.

One category involves the group of agents that act directly on the receptor site in the pituitary. This group includes agents such as apomorphine, bromocryptine, and piribedil. Because these agents are believed to act directly at the receptor site, the amount of agent needed to provide the desired activity is very small.

The second category of agents includes DOPA which is simply converted by endogenous enzymes to dopamine.

The last group of chemical agents influencing dopamine activity includes the compounds (I) of this invention, most notably mazindol, as well as amphetamine, cocaine, and methylphenidate. These compounds are believed to all act in a similar fashion, i.e., to increase the amount of dopamine available to the receptor by either releasing stored dopamine and/or blocking the reuptake of released dopamine (termed indirect action). Amphetamine was found to not significantly affect prolactin release [J. Pharm. Pharmac. 28, 643 (1976)] and this was later confirmed and shown to be true as well of methylphenidate and cocaine which caused a slight but significant suppression of prolactin release only at doses higher than required to produce the hypermotility associated with enhancement of the dopaminergic system [Life Sciences, 21, 267 (1977)]. In the case of amphetamine, the dose required to significantly affect prolactin secretion was shown to be 2–4 times the normal dose required for anorexia. The activity of the compounds (I) of this invention in inhibiting the secretion of prolactin is accordingly unexpected and surprising. Indeed, the dose of mazindol required to inhibit prolactin secretion has been shown to be about 100 times less than is required to produce anorexia with mazindol.

The compositions with which this invention are concerned, namely the compounds (I) alone or in combination with the secondary active agents, by inhibiting the secretion of prolactin, may accordingly be utilized in the treatment of conditions involving hyperprolactinemia, such as menstrual dysfunctions, e.g., ammenorrhea and galactorrhea, hypertension of mammary carcinoma associated with elevated serum prolactin levels, or they may be used in the treatment of serum prolactin levels, or they may be used in the treatment of conditions involving hypogonadism such as infertility and impotence, or in the regulation of postpartem lactation.

For use as prolactin inhibitors, compounds (I) either alone or in conjunction with the secondary active agents may be administered, preferably orally or parenterally, as such or admixed with conventional pharmaceutical carriers. They may be administered orally in such forms as tablets, dispersible powders, granules, or capsules, or as oral liquids, e.g., oral liquid suspensions, syrups, and elixirs, parenterally as solutions, suspensions, dispersions, emulsions, and the like, e.g., a sterile injectable aqueous suspension, and as suppositories, etc. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable exicpients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques or be otherwise prepared so as to delay disintegration and absorption in the gastrointestinal tract and thereby provide a sustained action over a longer period. Similarly, suspensions, syrups and elixirs may contain the active ingredient in admixture with any of the conventional exicpients utilized for the preparation of such compositions, e.g., suspending agents (methyl-cellulose, tragacanth and sodium alginate), wetting agents (lecithin, polyoxyethylene stearate and polyoxyethylene sorbitan mono-oleate) and preservatives (ethyl-p-hydroxybenzoate). Capsules may contain the active ingredient alone or admixed with an inert solid diluent, e.g., calcium carbonate, calcium phosphate and kaolin. The injectable compositions are formulated as known in the art and may contain appropriate dispersing or wetting agents and suspending agents identical or similar to those mentioned above. These pharmaceutical preparations may contain up to about 90% of the active ingredient in combination with the carrier or adjuvant.

Furthermore, the compounds of formula (I) and the secondary active agents may be similarly administered in the form of their corresponding non-toxic pharmaceutically acceptable acid addition salts. Such salts possess the same order of activity as the respective free base, are readily prepared by reacting the base with an appropriate acid and accordingly are included within the scope of the invention. Representative of such salts are the mineral acid salts, such as the hydrochloride, hydrobromide, sulfate, phosphate and the like and the organic acid salts, such as the succinate, maleate, fumarate, acetate, p-toluenesulfonate, and the like.

The dosage of active ingredient employed for inhibiting prolactin may vary depending on the particular compound (I) or the combination of compound (I) and the secondary active agents employed and the severity of the condition being treated.

However, in general, satisfactory results are obtained when the compounds (I) alone are administered, preferably orally, at a daily dosage of from about 0.01 milligram to about 5 milligrams per kilogram of animal body weight, preferably given in divided doses two to four times a day, or in sustained release form. For most large mammals, the total daily dosage is from about 0.005 to 0.5 milligrams. Dosage forms suitable for internal use comprise from about 0.00125 to about 0.25 milligrams of the active compound (I) in intimate admixture with a solid or liquid pharmaceutically acceptable carrier or diluent.

Generally, satisfactory results are obtained when using a combination of compound (I) and the secondary active agents when the combination is administered, preferably orally, such that (1) compounds (I) are administered at a daily dosage of from about 0.002 milligrams to about 2 milligrams per kilogram of animal body weight, and (2) the secondary active agents are administered at a daily dosage of 0.001 to about 250 milligrams per kilogram of animal body weight, with the preferred secondary active agent 2-bromo-α-ergocryptine being administered at a daily dosage of 0.01 milligrams to about 50 milligrams per kilogram of animal body weight, preferably given in divided doses two to four times a day, or in sustained release form; and for most large animals, the total daily dosage in the combination (1) for compounds (I) is from about 0.001 milligrams to about 0.2 milligrams, and (2) for the secondary active agents is from about 0.05 milligrams to about 50 milligrams, with the preferred secondary active agent 2-bromo-α-ergocryptine being administered at a total daily dosage of about 0.5 milligrams to about 5 milligrams.

Dosage forms of the combination product for internal use comprise from about 0.00025 milligrams to about 0.1 milligram of compound (I) and about 0.0125 milligrams to about 25 milligrams of secondary active agent, with the preferred secondary agent 2-bromo-α-ergocryptine being present to the extent of about 0.125 milligrams to about 2.5 milligrams, all in intimate admixture with a solid or liquid pharmaceutically acceptable carrier or diluent.

The preferred pharmaceutical compositions from the standpoint of preparation and ease of administration are tablets or capsules containing about 0.005 to 0.3 milligrams of active ingredient (I) alone and, when in combination, about 0.001 to 0.1 milligram of compound (I) plus about 0.5 to 3 milligrams of the secondary active agent.

EXAMPLES 1 AND 2

Tablets and Capsules Suitable for Oral Administration

Tablets and capsules containing the ingredients indicated below may be prepared by conventional techniques and are useful in inhibiting prolactin secretion at a dose of one tablet or capsule 2 to 4 times a day.

| INGREDIENT | WEIGHT (mg.) | |
|---|---|---|
| | Tablet | Capsule |
| 5-(p-chlorophenyl)-5-hydroxy-2,3-dihydro-5H-imidazo[2,1-a]isoindole | .01 | .01 |
| tragacanth | 10 | — |
| lactose | 246.5 | 298 |
| corn starch | 25 | — |
| talcum | 15 | — |
| magnesium stearate | 2.5 | — |

EXAMPLES 3 AND 4

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered in inhibiting prolactin excretion. The injectable suspension is suitable for administration once a day whereas the oral liquid suspension is suitably administered 2 to 4 times per day for this purpose.

| INGREDIENTS | WEIGHT (mg.) | |
|---|---|---|
| | Sterile injectable suspension | Oral Liquid suspension |
| 5-(p-chlorophenyl)-5-hydroxy 2,3-dihydro-5H-imidazo [2,1-a]isoindole | 0.1 | .02 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80) U.S.P. | — | 5 |
| sorbitol solution, 70% U.S.P. | — | 2,500 |
| buffer agent to adjust pH for desired stability | q.s. | q.s. |
| water | for injection q.s. to 1 ml. | q.s. to 5 ml. |

EXAMPLES 5 AND 6

Further Tablets and Capsules

Tablets and capsules containing the active ingredients below may be prepared by conventional techniques and are useful in inhibiting prolactin secretion at a dose of one tablet or capsule 2 to 4 times a day.

| INGREDIENT | WEIGHT (mg.) | |
|---|---|---|
| | Tablet | Capsule |
| mazindol | .005 | .005 |
| 2-bromo-α-ergocryptine | 1 | 2 |
| tragacanth | 10 | — |
| lactose | 246 | 297.5 |
| corn starch | 25 | — |
| talcum | 15 | — |
| magnesium stearate | 2.5 | — |

The compounds 5-(3,4-dichlorophenyl)-5-hydroxy-2,3-dihydro-5H-imidazo[2,1-a]isoindole, 5-(3-fluorophenyl)-5-hydroxy-2,3-dihydro-5H-imidazo[2,1-a]isoindole, 5-(p-fluorophenyl)-5-hydroxy-2,3,5,6-tetrahydroimidazo[2,1-a]isoquinoline, or 5-hydroxy-5-phenyl-2,3-dihydro-5H-imidazo[2,1-a]isoindole may be used in place of 5-(p-chlorophenyl)-5-hydroxy-2,3-dihydro-5H-imidazo[2,1-a]isoindole for these formulations of Examples 1 through 6, inclusive.

What is claimed is:

1. A method for inhibiting prolactin secretion which comprises administering to a mammal in need of said treatment an effective amount of a compound of the formula

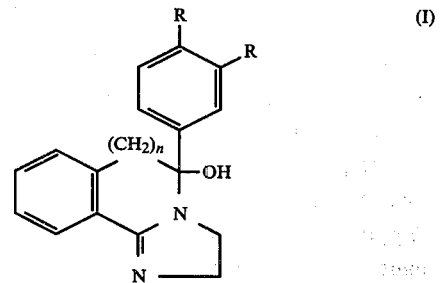

where
n represents 0 or 1,
each R, independently, represents hydrogen or halo of atomic weight about 19–36,
or a pharmaceutically acceptable acid addition salt thereof.

2. A method according to claim 1 wherein n represents 0.

3. A method according to claim 2 in which the compound is 5-(p-chlorophenyl)-5-hydroxy-2,3-dihydro-5H-imidazo[2,1-a]isoindole.

4. A method according to claim 2 wherein the compound is administered to a mammal in need of said treatment at a daily dose of from about 0.005 milligrams to about 0.5 milligrams.

5. A method according to claim 2 wherein the compound is administered to a mammal in need of said treatment in a unit dosage form comprising said compound to the extent of from about 0.00125 milligrams to about 0.25 milligrams per unit dosage.

6. A method for enhancing the prolactin secretion inhibition activity of chemical agents so active which comprises administering to a mammal in need of said treatment an effective amount of both said chemical agent and an effective amount of a compound of formula (I)

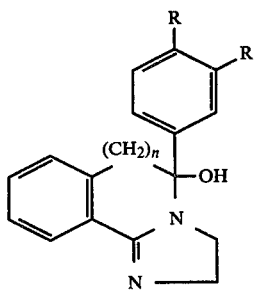

(I)

where
 n represents 0 or 1,
 each R, independently, represents hydrogen or halo of atomic weight about 19–36,
or a pharmaceutically acceptable acid addition salt thereof.

7. A method according to claim 6 where n represents 0.

8. A method according to claim 7 in which the compound of formula I is mazindol.

9. A method according to claim 8 in which the chemical agent active in inhibiting prolactin secretion is an ergocryptine, an ergoline, piribedil or an apomorphine.

10. A method according to claim 8 in which the chemical agent active in inhibiting prolactin secretion is ergocryptine, 2-bromo-α-ergocryptine, lergotrile, lisuride, 8α-cyanomethyl-6-methylergoline, 6-methyl-8β-(2-pyridylthiomethyl)-ergoline, 6-methyl-8α-(N,N-dimethylsulphamoylamino)-ergoline, piribedil or apomorphine.

11. A method according to claim 8 in which the chemical agent active in inhibiting prolactin secretion is 2-bromo-α-ergocryptine.

12. A method according to claim 11 wherein the mazindol is administered at a daily dose of 0.001 to 0.2 milligrams and the 2-bromo-α-ergocryptine is administered at a daily dose of 0.5 to 5 milligrams.

13. A pharmaceutical composition comprising effective amounts of a compound of the formula

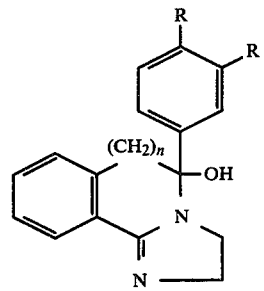

(I)

where
 n represents 0 or 1,
 each R, independently, represents hydrogen or halo of atomic weight about 19–36,
or a pharmaceutically acceptable acid addition salt thereof in combination with a secondary active agent itself useful in inhibiting prolactin secretion.

14. A pharmaceutical composition according to claim 13 wherein said compound of formula (I) is mazindol.

15. A pharmaceutical composition according to claim 14 wherein said secondary active agent is an ergocryptine, an ergoline, piribedil, or an apomorphine.

16. A pharmaceutical composition according to claim 14 wherein said secondary active agent is ergocryptine, 2-bromo-α-ergocryptine, lergotrile, lisuride, 8α-cyanomethyl-6-methylergoline, 6-methyl-8β-(2-pyridyl-thiomethyl)-ergoline, 6-methyl-8α-(N,N-dimethylsulphamoylamino)-ergoline, piribedil or apomorphine.

17. A pharmaceutical composition according to claim 14 wherein said secondary active agent is 2-bromo-α-ergocryptine.

18. A pharmaceutical composition according to claim 13 in a unit dosage form comprising said compound of formula I to the extent of about 0.001 milligrams to about 0.1 milligrams and said secondary active agent to the extent of 0.5 milligrams to about 3 milligrams.

19. A pharmaceutical composition according to claim 18 wherein said unit dosage form comprises mazindol and 2-bromo-α-ergocryptine.

20. A method for inhibiting prolactin secretion which comprises administering to a mammal in need of said treatment a daily dose of from 0.005 milligrams to about 0.5 milligrams of mazindol.

21. A method for inhibiting prolactin secretion which comprises administering to a mammal in need of said treatment a unit dosage of mazindol comprising said compound to the extent of from about 0.00125 milligrams to about 0.25 milligrams per unit dosage.

* * * * *